United States Patent [19]

Feldman et al.

[11] Patent Number: 5,056,020
[45] Date of Patent: Oct. 8, 1991

[54] METHOD AND SYSTEM FOR THE CORRECTION OF IMAGE DEFECTS OF A SCANNER DUE TO THE MOVEMENTS OF THE LATTER

[75] Inventors: Andréi Feldman, Paris; Dominique Cornuejols, Palaiseau, both of France

[73] Assignee: General Electric CGE SA, Issy-les-Moulineaux, France

[21] Appl. No.: 406,039

[22] Filed: Sep. 12, 1989

[30] Foreign Application Priority Data

Sep. 16, 1988 [FR] France .................. 88 12120

[51] Int. Cl.$^5$ .................................... G06F 15/00
[52] U.S. Cl. ..................... 364/413.19; 378/4; 364/413.14; 364/413.15
[58] Field of Search .......... 378/4; 364/413.19, 413.14, 364/413.15

[56] References Cited

U.S. PATENT DOCUMENTS

| | | | |
|---|---|---|---|
| 4,068,306 | 11/1978 | Chen et al. ............. | 364/413.15 |
| 4,135,096 | 1/1979 | Giordano ................ | 364/413.15 |
| 4,144,569 | 3/1979 | Wagner .................. | 364/413.19 |
| 4,217,641 | 8/1980 | Naparstek .............. | 364/413.19 |
| 4,272,820 | 6/1981 | Lux ....................... | 364/413.19 |

FOREIGN PATENT DOCUMENTS 0218367  4/1987  European Pat. Off. .

*Primary Examiner*—Jerry Smith
*Assistant Examiner*—Laura Brutman
*Attorney, Agent, or Firm*—Oblon, Spivak, McClelland, Maier & Neustadt

[57] ABSTRACT

Disclosed is a method for the correction, in a scanner, of the defects due to the movements of the scanner. The method consists in having a rod which introduces a major attenuation and causing the scanner to make a full turn around a center of rotation O and obtaining m distinct views of the rod, each corresponding to an angular position $\alpha_j$. The analysis of the signals of each view enables determining the angle $\beta_j$ of the rod. The knowledge of this angle $\beta_j$ leads to the computation of the coordinates b and c of the rod and the theoretical value $\beta_{th}$ of the angle $\beta$ for each view. The difference between the theoretical value $\beta_{th}$ and the measured value $\beta_j$ is used in the device for processing the scanner image.

5 Claims, 2 Drawing Sheets

METHOD AND SYSTEM FOR THE CORRECTION OF IMAGE DEFECTS OF A SCANNER DUE TO THE MOVEMENTS OF THE LATTER

BACKGROUND OF THE INVENTION

1. Field of the Invention

The invention concerns X-ray scanners and, more particularly, a method enabling the correction, in the the images obtained, of the defects due to the movements of the measurement set. It also concerns a system for the correction of defects such as this.

2. Description of the Prior Art

To examine patients, increasing use is being made of X-ray machines called "scanners" which take cross-sectional views of a patient. These machines are based on the physical phenomenon of the absorption of X-rays by the human body. This absorption is directly related to the distance x travelled by X-rays in the body, according to the formula:

$$I = I_o e^{-bx}$$

wherein:

$I_o$ is the intensity of the radiation entering the human body,

I is the intensity of radiation leaving the human body, b is a coefficient of attenuation that depends on the body crossed. In a logarithmic scale of measurement, the attenuation $I/I_o$ is equal to bx, i.e. it is proportional to the distance x. These machines consist essentially, as shown in figure 1, of an X-ray source 10 associated with a detection device 11, these two elements being arranged with respect to each other in a fixed geometrical relationship so that the body to be examined can be interposed between them. Furthermore, they are supported by a structure (not shown) which can rotate around the body to be examined so as to irradiate the body along different angles. The X-ray source, which is controlled by a device 13, emits rays according to an angular sector with a width that is sufficient to illuminate the entire cross-section of the body. The detection device 11 is shaped like an annular sector, the length of this sector being adapted to the width of the X-ray beam and being formed by a large number of elementary detectors 12, juxtaposed beside one another.

To obtain an image of the cross-section of the human body through which the X-ray beam travels, the supporting structure of the source 10 and of the detection device 11 is made to rotate on the body, and the output signals of the elementary detectors 12 are measured so as to process them appropriately according to known methods in order to draw therefrom an image representing the cross-section. For this processing operation, the elementary detectors 12, also called channels, are connected to an electronic device 14 which first of all computes the logarithm of the signals received so as to obtain a signal, the amplitude of which is proportional to the attenuation of the X-rays. The axis of rotation of the structure formed by the source 10 and the detection device 11 is located at the point 0, which means that the source 10 and the detectors 12, each describes during the rotation of the structure, a circumference having a center 0 and a known radius. This is true only in theory, for the manufacturing and using tolerances lead to deviations from the theoretical positions. The result thereof is defects, called "artefacts", in the images and a decrease of the spatial resolution.

An aim of the present invention, therefore, is to implement a method that enables correcting the defects resulting from deviations in the positions of the source and the detectors with respect to their theoretical position.

Another aim of the invention is to achieve a system implementing said method of correction.

SUMMARY OF THE INVENTION

The invention relates to a method for the correction of defects in images of a scanner, due to movements by the latter, said method comprising the following operations:

the positioning of at least one rod which introduces a major weakening or attenuation in the incident X-radiation, the rotation of the scanner by a full turn so as to achieve a number m of views on the N detectors or channels of the scanner, each view corresponding to a determined angular section $\alpha_j$ of the scanner around its center of rotation;

the determining, for each view, of the center of gravity of the attenuation (rod) so as to measure an angle $\beta_j$ between the axes of radiation, one of which goes through the center of rotation and the other through the center of gravity of the attenuation;

the measurement of the Cartesian coordinates b and c of the center of gravity of the attenuation, namely of the rod, the computation, for each view, of the theoretical angle $\beta_{th}$ between the axes of radiation, one of which and the other through the point having coordinates b and c;

the computation, for each view, of the difference $\delta_j$ between the angles $\beta_{th}$ and $\beta_j$ and the memorizing of the m values $\delta_j$, each value $\delta_j$ being then used to modify the corresponding value of the angular position $\alpha_j$.

The invention also pertains to a system to implement the above-described method in a scanner comprising a source of X-radiation, a device to detect the X-radiation with N detectors, means to make the X-radiation source and the detection device rotate around a center of rotation, means to introduce at least one rod between the X-radiation source and the X-radiation detection device, means to record, in a memory, the received signals corresponding to m different angular positions $\alpha_j$ of the source and the detection device during a full rotation, said system further comprising:

first means associated with the memory to analyze the signals contained in said memory, so as to determine, for each view, the value of the angle $\beta_j$, second means associated with the memory to analyze the signals contained in said memory so as to determine the coordinates b, c of the rod, third means to compute the theoretical angle $\beta_{th}$ for each of the m angular positions $\alpha_j$, fourth means to compute, for each of the m views, the angular difference:

$$\beta_{th} - \beta_j = \delta_j, \text{ and}$$

fifth means to record the m angular correction values $\delta_j$.

BRIEF DESCRIPTION OF THE DRAWINGS

Other features and advantages of the present invention will emerge from the following description of a particular exemplary embodiment, said description being made with the appended drawings wherein.

DESCRIPTION OF PREFERRED EMBODIMENTS

Figure 1:
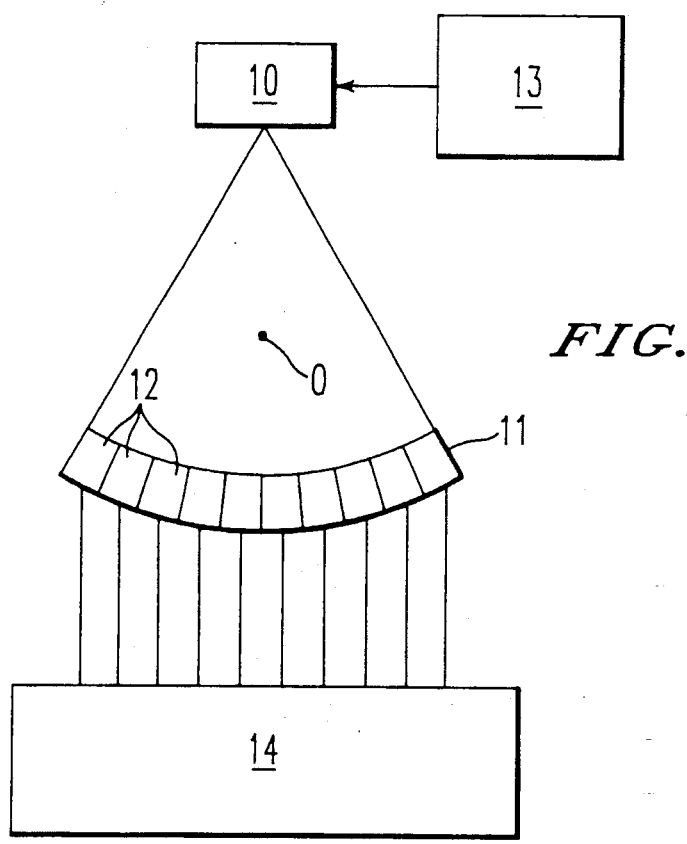
FIG. 1 is a schematic drawing of an X-ray scanner.
Figure 2:
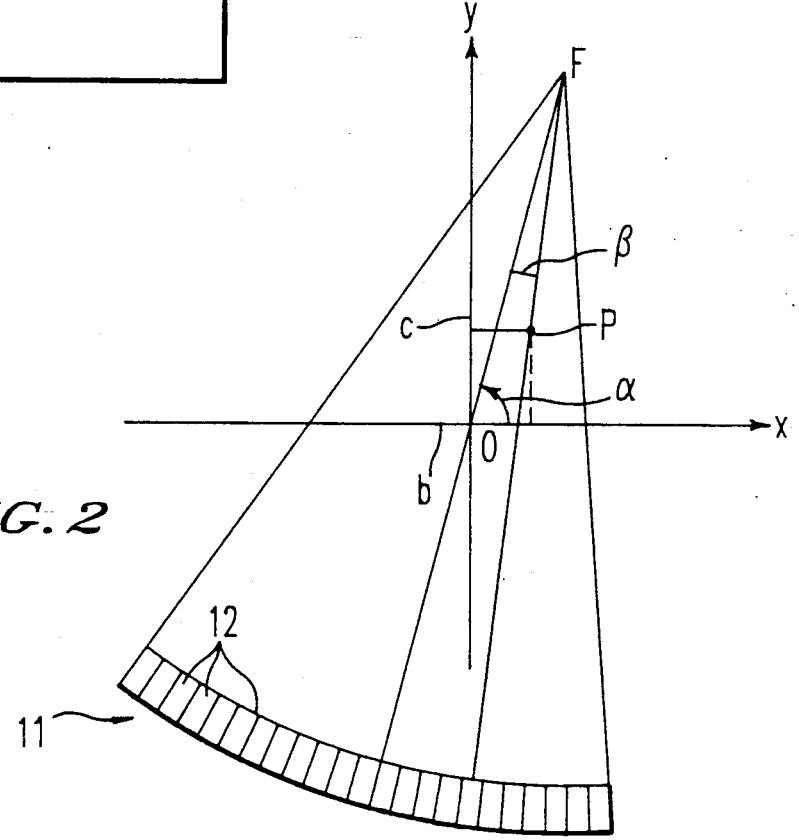
FIG. 2 is a geometrical diagram enabling an understanding of the method implemented.

The geometrical diagram of FIG. 2 enables a better understanding of the method and makes it possible to determine the corrections to be made. In this figure, the point O designates the axis of rotation of the scanner, and the axes Ox and Oy are two axes that are orthogonal to each other and to the axis of rotation. Of these two axes, one Ox is horizontal and the other Oy is vertical. The angular position of the structure is defined by the angle $\alpha$ made by the straight line FO with Ox, with F marking the focus of the X-ray source. The point P indicates the location of a rod that absorbs X-radiation to a high degree and has coordinates which are, for example, b on the x axis and c on the y axis. Furthermore, $\beta$ shall designate the angle OFP. This angle varies during one rotation cycle of the scanner. This angle can also be defined as being the angle between the central detector (aligned with FO) of the detection device 11 and the order i detector, the signal of which is attenuated by the rod P. Thus, for each order j view, several channels will have a signal highly attenuated by the rod P, thus enabling an angle $\beta_j$ to be defined. According to the invention, this angle $\beta_j$ will be compared by subtraction to the theoretical angle $\beta_{th}$ defined by the trigonometrical relationship:

$$\beta_{th} = \arctg \frac{OF \sin \alpha_j - c}{OF \cos \alpha_j - b} - \alpha_j \qquad (1)$$

It is the result of this subtraction $\beta_{th} - \beta_j$ which shall be used to make corrections on the angular positions $\alpha_j$. To know $\beta_{th}$, it is necessary, firstly, to determine the coordinates b and c of the rod P, which can be obtained in different ways, for example by performing an acquisition on the rod leading to a measurement of b and c on the image obtained. Another way to compute b and c shall be explained further below in relation to the description of FIG. 3. The angle $\beta_{th}$ is then computed by the formula (1).

For each view j, the angle $\beta_j$ is determined by the position of the channel i which has the most attenuated signal, the one corresponding to the X-rays that encounter the rod P.

The method used to correct the image defects of a scanner due to the movements of the latter therefore comprises the following operations:

the positioning of at least one rod introducing a major weakening or attenuation in the incident X-radiation, the rotation of the scanner on a complete turn so as to achieve a number m of views on the N detectors or channels, each view corresponding to a determined angular position $\alpha_j$ of the scanner around its center of rotation, the determining, for each order j view (angle $\alpha_j$) of the center of gravity of the attenuation (corresponding to the rod P), thus obtaining the value of the angle $\beta_j$, the measurement of the coordinates b and c of the rod P, the computation for each view j of the theoretical angle $\beta_{th}$ using the measured coordinates b and of the rod in using the formula (1), the computation, for each view j, of the difference $$\delta_j = (\beta_{th} - \beta_j)$$

which forms a correction value, and the memorizing of m values $\delta_j$, the use of each value $\delta_j$ to modify the corresponding value of the angular positions of N detectors for the order j view.

Figure 3:
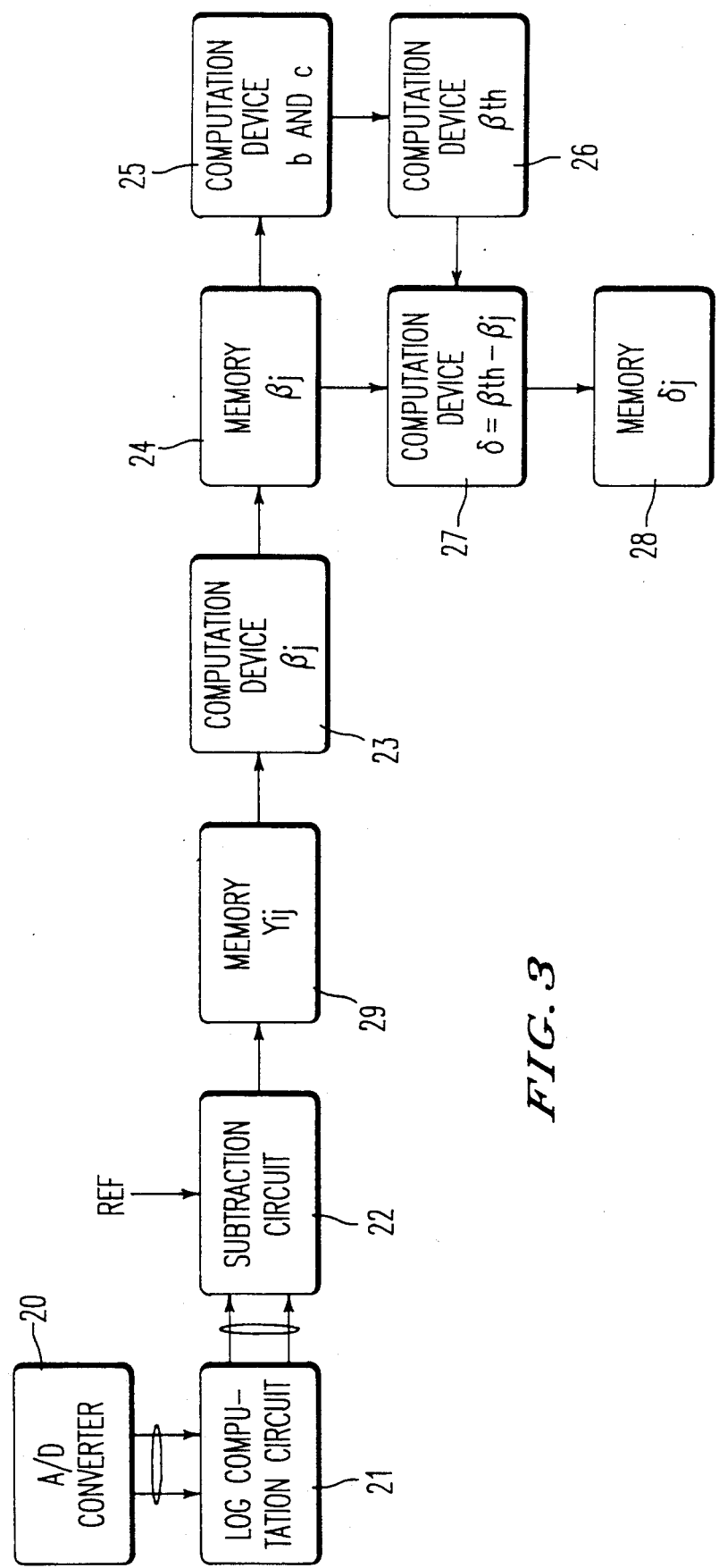
FIG. 3 is a block diagram of a system for the processing of the signals of the detectors, implementing the method for the correction of the images of a scanner according to the invention.

To implement this method of correction, the invention proposes a system which shall now be described in relation to FIG. 3. It comprises an analog/digital converter 20 to which the output signals of the N detectors or channels of the detection device 11 are applied. The N digital codes, corresponding to an order j position or view are applied to a logarithm computation circuit 21 which gives, for each channel i and each view j, a code representing the attenuation undergone by the X-radiation. The N codes resulting from this logarithmic computation operation are applied to a subtraction circuit 22 in which a value REF is subtracted from them. This value REF represent the attenuation undergone by the X-radiation in the air. This value is obtained by means of a detector called a monitor, having a position on the detection device 11 such that it receives the X-radiation without attenuation. The codes that result from this subtraction, called $Y_{ij}$ measurements, are recorded in a memory 29 and then processed in a computing device 23 in order to determine, for each view j, the angle $\beta_j$ corresponding to the rod P. This is done, for example, by analyzing the N signals $Y_i$ of each view to determine the channel i that represents the center of gravity of the attenuation due to the rod P. More precisely, the channels corresponding to signals attenuated by the rod P are determined; the maximum value of this attenuation does not necessarily correspond to the exact angular position of a channel. In other words, the straight line FP is not as a rule aligned with the center of a detector 12 (FIG. 2). Hence it is necessary to determine the maximum attenuation, and a value of i is then obtained. This value i is not a integer but a fractional number. The angle $\beta_j$ is then computed by the number of channels or detectors 12 between the central detector, aligned with FO, and the order i detector (i being a fractional number) corresponding to the maximum attenuation, in taking into account the fact that the detectors are evenly arranged on an arc of a circle with a center F.

The m values $\beta_j$ are recorded in a memory 24 in order to be used, firstly, to compute the coordinates b and c, and, secondly, to obtain the correction values $\delta_j$. The computation of b and c is done in a circuit 25 by using the formula (1) in which $\beta_{th}$ is replaced by $\beta_j$ measured. More precisely, the successive values of $\beta_j$ are used two by two so that, each time, a system of two equations is obtained with two unknown values b and c, wherein $\beta_j$ and $\alpha_j$ are known. Each system of equations is of the type:

$$\beta_j = \arctg \frac{OF \sin \alpha_j - c_j}{OF \cos \alpha_j - b_j} - \alpha_j$$

$$\beta_{j+1} = \text{arctg} \frac{OF \sin \alpha_{j+1} - c_j}{OF \cos \alpha_{j+1} - b_j} - \alpha_{j+1}$$

with j varying from 1 to m so as to obtain m/2 systems of equations. It will be understood that $\beta_{m+1}$ actually corresponds to $\beta_1$.

The resolving of the m/2 systems results in m/2 values of b and m/2 values of c for which the mean values are computed.

It is these mean values of b and c that are transmitted to a circuit 26 which achieves, for each position view $\alpha_j$, the computation of the m theoretical values $\beta_{th}$. Each of the m values $\beta_j$ contained in the memory 24 is algebraically subtracted in the circuit 27 from the corresponding value (same angle $\alpha_j$, i.e. same view) given by the computation circuit 26. We then obtain m differential values $\delta_j$ which are recorded in a memory 28 so as to be used in the image processing device by modifying the angles $\alpha_{ij}$ which indicate the angular positions of the detectors with respect to the axis Ox. The invention has been described with reference to the use of a single rod, but it can also be implemented in using several rods with different positions.

The system described with reference to FIG. 3 can be achieved according to different ways without going beyond the scope of the present invention. Notably, the memory 29 which records the values $Y_{ij}$ can be eliminated if the computation of $\beta_j$ (circuit 23) is done in real time.

Similarly, the coordinates b and c of the rod P can be computed in different ways, for example on the image of the rod obtained by the scanner as indicated above.

In addition, the method and the system can be implemented by using more than one rod so as to determine a mean value for $\delta_j$.

What is claimed is:

1. A method for the correction of defects in images of a scanner, due to movements by the latter, said method comprising the following operations:

the positioning of at least one rod which introduces a major weakening or attenuation in the incident X-radiation, the rotation of the scanner by a full turn so as to achieve a number m of views on the N detectors or channels of the scanner, each view corresponding to a determined angular section $\alpha_j$ of the scanner around its center of rotation;

the determining, for each view, of the center of gravity of the attenuation (rod) so as to measure an angle $\beta_j$ between the axes of radiation, one of which goes through the center of rotation and the other through the center of gravity of the attenuation;

the measurement of the Cartesian coordinates b and c of the center of gravity of the rod, the computation, for each view, of the theoretical angle $\beta_{th}$ between the axes of radiation, one of which goes through the center of rotation of the scanner, and the other through the point of coordinates b and c;

the computation, for each view, of the difference $\delta_j$ between the angles $\beta_{th}$ and $\beta_j$ and the memorizing of the m values $\delta_j$, each value $\delta_j$ being then used to modify the corresponding value of the angular position $\alpha_j$.

2. A method according to claim 1, wherein the operation for determining the angle $\beta_j$ consists in analyzing, for each view, the N signals received so as to determine the angular position of the center of gravity of the weakest signal and to compare it with the angular position corresponding to the alignment between the focus of the X-radiation and the center 0 of rotation of the scanner.

3. A method according to claim 1 or 2, wherein the operation for the measurement of the Cartesian coordinates b and c of the rod is done with the m values $\beta_j$ in resolving m/2 systems of two equations with two unknown quantities of the type $$\beta_j = \text{arctg} \frac{OF \sin \alpha_j - c_j}{OF \cos \alpha_j - b_j} - \alpha_j$$

and $$\beta_{j+1} = \text{arctg} \frac{OF \sin \alpha_{j+1} - c_j}{OF \cos \alpha_{j+1} - b_j} - \alpha_{j+1}$$

(with j varying from 1 to m) and in computing the mean values of the m/2 values obtained for b and c.

4. A method according to claim 1 or 2, wherein the operation of the computation for each view of the theoretical angle $\beta_{th}$ is done according to the formula:

$$\beta_{th} = \text{arctg} \frac{OF \sin \alpha_j - c}{OF \cos \alpha_j - b} - \alpha_j$$

5. A system to implement the method according to claim 1 or 2 in a scanner comprising a source of X-radiation, a device to detect the X-radiation with N detectors, means to make the X-radiation source and the detection device rotate around a center of rotation, means to record, in a memory, the received signals corresponding to m different angular positions $\alpha_j$ of the source and the detection device during a full rotation, said system further comprising:

first means associated with the memory to analyze the signals contained in said memory, so as to determine, for each view, the value of the angle $\beta_j$, second means to determine the coordinates b, c of the rod, third means to compute the theoretical angle $\beta_{th}$ for each of the m angular positions $\alpha_j$, fourth means to compute, for each of the m views, the angular difference:

$\beta_{th} - \beta_j = \delta_j$, and fifth means to record the m angular correction values $\delta_j$.

* * * * *